(12) United States Patent
Sevenster et al.

(10) Patent No.: US 12,057,236 B2
(45) Date of Patent: *Aug. 6, 2024

(54) ECHOCARDIOGRAM CONTEXT MEASUREMENT TOOL

(71) Applicant: KONINKLIJKE PHILIPS N.V., Eindhoven (NL)

(72) Inventors: Merlijn Sevenster, Haarlem (NL); Thomas Andre Forsberg, Hayward, CA (US); Amit Patel, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/870,909

(22) Filed: Jul. 22, 2022

(65) Prior Publication Data

US 2022/0367068 A1   Nov. 17, 2022

Related U.S. Application Data

(63) Continuation of application No. 16/489,367, filed as application No. PCT/EP2018/054854 on Feb. 28, 2018, now Pat. No. 11,437,149.

(60) Provisional application No. 62/465,177, filed on Mar. 1, 2017.

(51) Int. Cl.
| | | |
|---|---|---|
| *G16H 70/20* | (2018.01) | |
| *A61B 8/00* | (2006.01) | |
| *A61B 8/08* | (2006.01) | |
| *A61B 8/14* | (2006.01) | |
| *G16H 30/40* | (2018.01) | |

(52) U.S. Cl.
CPC ........... *G16H 70/20* (2018.01); *A61B 8/0883* (2013.01); *A61B 8/14* (2013.01); *A61B 8/465* (2013.01); *A61B 8/469* (2013.01); *A61B 8/5223* (2013.01); *A61B 8/5292* (2013.01); *G16H 30/40* (2018.01)

(58) Field of Classification Search
CPC ...... G16H 70/20; G16H 30/40; A61B 8/0883; A61B 8/14; A61B 8/469; A61B 8/5223; A61B 8/5292
See application file for complete search history.

(56) References Cited

U.S. PATENT DOCUMENTS

| | | | |
|---|---|---|---|
| 2006/0116577 A1* | 6/2006 | DeWitt | ..................... A61B 8/00 600/437 |
| 2008/0119718 A1 | 5/2008 | Hundley | |
| 2008/0137929 A1* | 6/2008 | Chen | ....................... G06T 17/20 382/131 |
| 2013/0345563 A1 | 12/2013 | Stuebe | |
| 2014/0181716 A1 | 6/2014 | Merritt | |
| 2014/0309530 A1 | 10/2014 | Chono | |

(Continued)

FOREIGN PATENT DOCUMENTS

JP    6055565 B1    12/2016

OTHER PUBLICATIONS

International Search Report and Written Opinion Dated May 30, 2018 for International Application No. PCT/EP2018/054854 Filed Feb. 28, 2018.

*Primary Examiner* — John D Li

(57) ABSTRACT

A system (100) includes an echocardiogram measurement tool (150) that determines a subset (152) of measurements from a list of echocardiogram measurements according to a view of an ultrasound imaging sequence (110) and a mapping (154) between the view and the subset of measurements.

16 Claims, 3 Drawing Sheets

(56) References Cited

U.S. PATENT DOCUMENTS

| | | | |
|---|---|---|---|
| 2017/0007161 A1* | 1/2017 | Zou | A61B 8/08 |
| 2017/0235903 A1* | 8/2017 | McLaughlin | A61B 8/461 |
| | | | 715/708 |
| 2017/0360402 A1* | 12/2017 | de Jonge | A61B 8/06 |
| 2019/0125298 A1* | 5/2019 | Abolmaesumi | A61B 8/4405 |

* cited by examiner

ECHOCARDIOGRAM CONTEXT MEASUREMENT TOOL

CROSS REFERENCE TO RELATED APPLICATIONS

This application a Continuation of U.S. patent application Ser. No. 16/489,367 filed Aug. 28, 2019, which is the U.S. National Phase application under 35 U.S.C. § 371 of International Application No. PCT/EP2018/054854 filed Feb. 28, 2018, which claims the benefit of U.S. Provisional Patent Application No. 62/465,177 filed Mar. 1, 2017. These applications are hereby incorporated by reference herein.

FIELD OF THE INVENTION

The following generally relates to ultrasound echocardiograms, and more specifically to echocardiogram measurements.

BACKGROUND OF THE INVENTION

Echocardiograms are performed to monitor and diagnosis heart disease and/or heart condition. A system that performs echocardiograms typically uses ultrasound (US) waves to create imaging sequences of a functioning heart with a probe that generates the ultrasound waves and detects reflected ultrasound waves.

US imaging sequences can include two dimensional (2-D) images, three-dimensional (3-D) images, Doppler imaging techniques, combinations and the like. An echocardiogram can include a multitude of sequences. Each sequence is typically an image of a portion of the heart over a cycle or at a phase.

The orientation of the probe relative to the heart determines the content of the image or view. The orientation of the probe relative to the heart includes a position and an angle of the probe on the skin of a patient, and thus, a direction of the waves relative to the heart and the portion of the heart included in the view. Views can include sub-views, which are minor adjustments in position and/or angle of the probe that focus on particular anatomical portions of the heart.

Measurements are made using the imaging sequence to quantify an aspect of an anatomical portion of the heart. The measurements are quantified, such as functions of a length, a width, a diameter, an area, a volume, combinations and the like. The measurements can be made at a specific phase of a cardiac cycle represented in the sequence. The anatomical portion measured can include aspects of an atrium, a ventricle, a vessel, a valve, and the like.

In quantifying aspects of the echocardiogram, a healthcare practitioner selects a measurement from a list of measurements that pertain to echocardiograms. The list of measurements, typically ordered alphabetically, can include over two hundred different measurements. The list can be very large even using abbreviations, such as LV for left ventricle, MV for mitral value, and the like. For example, in a display screen of an echocardiogram system, the abbreviated list can fill half the screen, temporarily obscuring half of the information concerning the echocardiogram.

SUMMARY OF THE INVENTION

Aspects described herein address the above-referenced problems and others.

The following describes embodiments of a system and method for a contextual based list of echocardiogram measurements. The context is determined from a view or sub-view of an echocardiogram imaging sequence and a mapping between the view or sub-view, anatomy displayed within the view or sub-view, and an echocardiogram measurement corresponding to the displayed anatomy. In some embodiments, the mapping includes further context according to usability statistics. In some embodiments, autonomous measurements are applied according to the context. In some embodiments, the view or sub-view is determined from analysis of the echocardiogram imaging sequence.

In one aspect, a system includes an echocardiogram measurement tool that determines a subset of measurements from a list of echocardiogram measurements according to a view of an ultrasound imaging sequence and a mapping between the view and the subset of measurements.

In another aspect, a method includes determining a subset of measurements from a list of echocardiogram measurements according to a view of an ultrasound imaging sequence and a mapping between the view and the subset of measurements.

In another aspect, a non-transitory computer-readable storage medium carrying instructions controls one or more processors to determine a subset of measurements from a list of echocardiogram measurements according to a view of an ultrasound imaging sequence and a mapping between the view and the subset of measurements These and other aspects of the invention will be apparent from and elucidated with reference to the embodiment(s) described hereinafter.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 3 flowcharts an embodiment of a method of context based view of echocardiogram measurements.

DETAILED DESCRIPTION OF EMBODIMENTS

Figure 1:
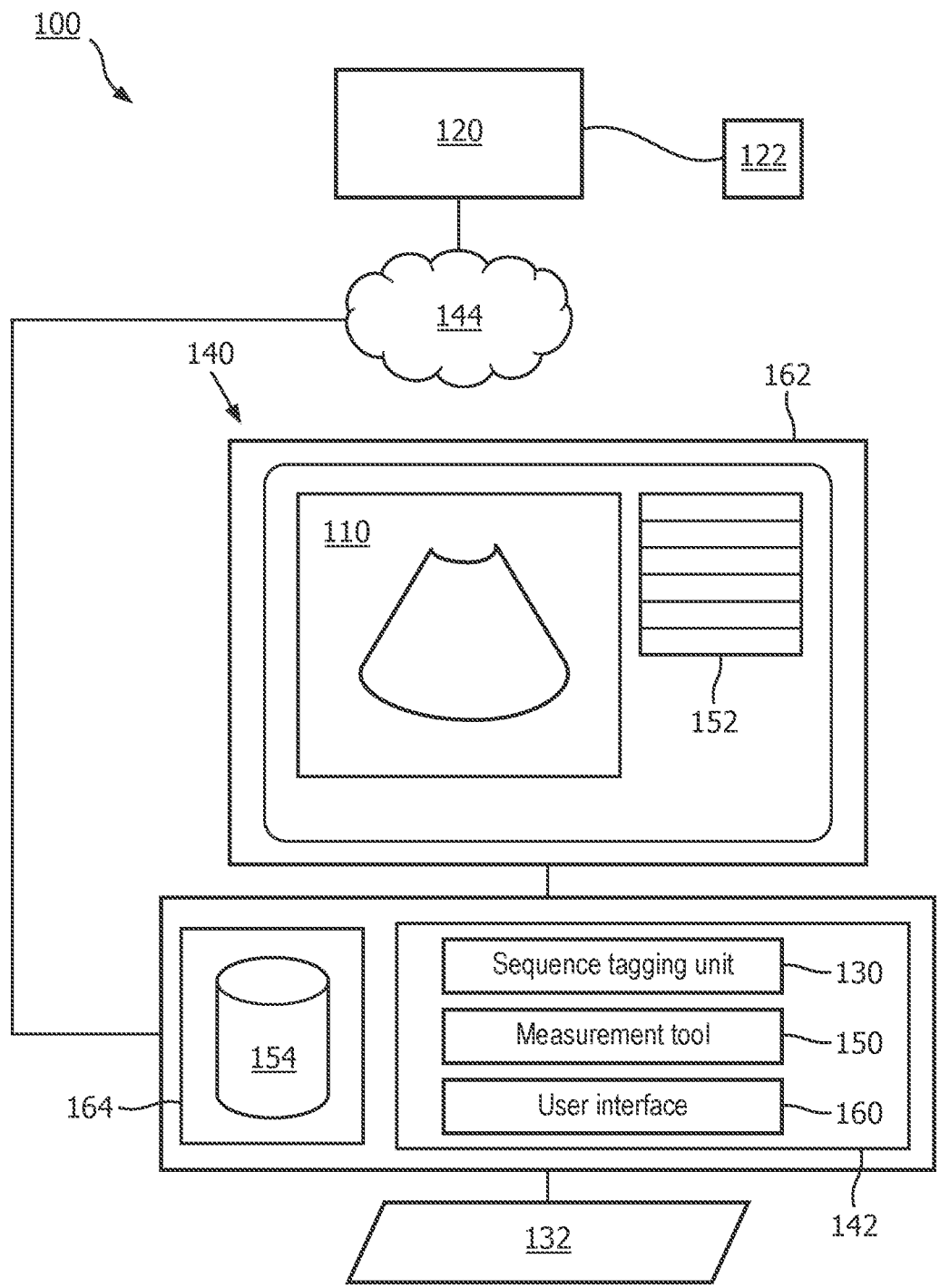
FIG. 1 schematically illustrates an embodiment of a system for context selected measurements of echocardiogram sequences.

With reference to FIG. 1, an embodiment of a system 100 for context selected measurement of an echocardiogram ultrasound sequence 110 is illustrated. An ultrasound (US) imaging scanner 120 scans a subject using a probe 122 and generates the sequence 110. The sequence 110 is an ultrasound image generated from a view determined by the operation of the probe 122 relative to the heart of the subject. The view determines anatomical portions of the heart present in the sequence 110.

The view can be represented as a single data element or include a sub-view and be represented as a combined data element. The sub-view can be nested at different levels N>1. For example, a first sub-view 1 of view PLAX includes sub-views A and B, which identify the views of PLAX, PLAX1, PLAX1A, and PLAX1B. PLAX1, as an intermediate nested, level, can be omitted. Views can be represented by textual explanations, numerical references, or combinations thereof. For example views can represented by textual explanations or abbreviations, such as Parasternal long axis (PLAX), Parasternal short axis (PSAX), Apical four chamber (AP4), Apical five chamber (AP5), Apical two chamber (AP2), Apical three chamber (AP3), Sub costal (SC), and Supra sternal notch (SSN). In another example, PLAX3 represents a combination of textual and numerical representation that includes a sub-view.

A sequence tagging unit 130 determines the view from an analysis of the sequence 110. The analysis can include pattern matching of the pixel data with reference images. The analysis can include segmentation of anatomical features and comparison with an anatomical model. In some embodiments, tagging can include, via a console or computing device 140, an entry of a view, a selection of a view, a display of the view and a modification of the view, combinations thereof and the like.

The computing device 140 or console can be part of, combined with, or separated from the US imaging scanner 120. The computing device 140 includes one or more processors 142, such as a digital processor, a microprocessor, an electronic processor, an optical processor, a multiprocessor, a distribution of processors including peer-to-peer or cooperatively operating processors, client-server arrangement of processors, and the like. The arrangement can include a network 144, which can include a bus structure or other internal or local communication structure, wireless or wired communications, public or private network communications, cellular or data communications, combinations thereof and the like. The computing device 140 can be configured as a laptop computer, a desktop computer, a tablet, a smartphone, a body worn device, and the like.

An echocardiogram measurement tool 150 determines a subset 152 of measurements from a list of echocardiogram measurements according to the view of the sequence 110 and a mapping 154 between the view and the subset 152 of measurements. For example in a PLAX3 view, measurements, such as left ventricular ejection fraction (LVEF), are included in the subset 152, while measurements, such as a diameter of the inferior vena cava (IVC Diam), are excluded from the subset 152. That is, the PLAX3 view is mapped to LVEF and is not mapped to IVC Diam. The PLAX3 view includes the anatomical portions of the left ventricle sufficient to compute the LVEF. The PLAX3 excludes the anatomical portions of the inferior vena cava sufficient to compute the IVC Diam and thus, the IVC Diam is not mapped according to the PLAX3 view. The mappings are determined according to the anatomy present in a view, and the anatomy with which the measurements are performed.

The mapping of echocardiogram measurements 154 can be represented and stored as a lookup table with data elements of a view and a measurement. For example, a table can include rows, each row representing a measurement according to a view. A view can include multiple measurements. Data elements or columns include the view and the corresponding measurement. The table can include other elements of the mapping, such as the anatomical portion according to the view to which the measurement applies, a link to the specific measurement for programmatic access, and the like.

A user interface 160 displays the sequence 110 and the determined subset 152 of measurements in a selectable list, such as in a menu, in a drop-down box, in a pick list, and the like on a display device 162. In some embodiments, the subset 152 is displayed at the top of the entire list of echocardiogram measurements showing the subset 152 on top of all possible measurements. In some embodiments, the remainder of measurements in the entire list of echocardiogram measurements (excluding the subset 152) are shown in a sub-menu or expansion box. That is, the entire list can be accessed through a sub-menu or expansion box. The sub-menu or expansion box does not display the remainder of the measurements until invoked, which, in some instances, does not obscure portions of the display. In some embodiments, individual measurements in the subset 152 are shown as active and those not included in the subset 152 are shown inactive, such as grayed out and non-selectable. In some instances, the displayed subset of measurements significantly shortens the number of displayed measurements, which covers less of the display 162 and reduces the number of measurements a healthcare practitioner searches to select a measurement. The display device 162 is suitably embodied by a computer display, smartphone display, projector, body worn display, and the like.

An input device 132, such as a keyboard, mouse, microphone, and the like, sends an input indicative of a selected measurement, such as an input indicative of a measurement in the displayed subset 152. The measurement tool 150, in response to the input, measures an aspect of the heart in the view according to the selected measurement. For example, in response to a mouse click selecting a left ventricle ejection fraction, the measurement tool measures the left ventricle ejection fraction according to the sequence 110.

In some embodiments, the measurement tool 150 autonomously selects and applies a measurement from the subset 152 of measurements to the tagged view prior to display by the user interface 160. The measurement from the subset 152 can be autonomously selected according to site policies or usability statistics, such as frequency of use by a healthcare practitioner, frequency of use by a group of practitioners, percentage of echocardiogram usage, percentage of sequence usage, threshold number of uses, and the like. For example, prior to display of the sequence 110, a measurement applied with a high frequency can be selected and applied by the measurement tool 150. The measured value can be included in the initial display of the sequence 110 or added to the display without the input for selecting the measurement from the list. In some embodiments, the autonomously selected and applied measurements are indicated with an icon or other symbol in the displayed subset.

The computer device 140 includes the processor 142 and a memory 164. The mapping 154 is suitably embodied by a configured electronic storage medium, such as local disk, cloud storage, server storage, remote storage and the like, accessed by the configured processor 142. The configured electronic storage medium can include system file structures, relational and/or object oriented database system structures, data structures, and the like.

The sequence tagging unit 130, the measurement tool 150 and the user interface 160 are suitably embodied by the processor 142, configured to receive the sequence 110, determine the view, generate the subset 152, display the sequence 110 and the subset 152, receive a selection and perform the measurement according to the selection.

The configured processor 142 executes at least one computer readable instruction stored in the computer readable storage medium 164, such as an optical disk, a magnetic disk, semiconductor memory of a computing device with the configured processor, which excludes transitory medium and includes physical memory and/or other non-transitory medium to perform the disclosed techniques. The configured processor may also execute one or more computer readable instructions carried by a carrier wave, a signal or other transitory medium. The lines between components represented in the diagram represent communications paths.

Figure 2:
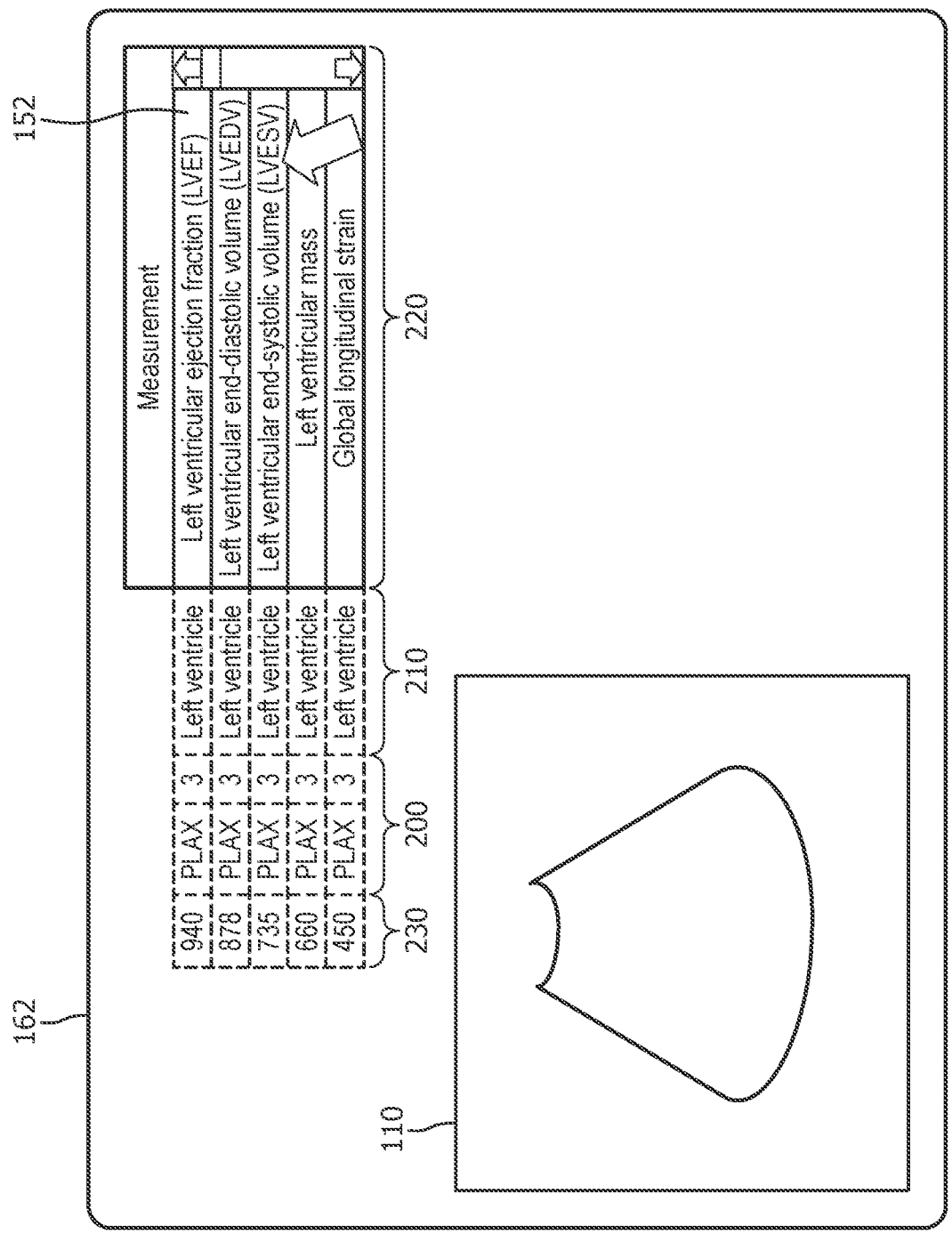

With reference to FIG. 2, an example of a displayed echocardiogram sequence 110 with a context based view of measurements that is a subset 152 of the list of echocardiogram measurements is illustrated. The context is based on the determined view of the sequence 110, such as PLAX. The determined view can include subviews. That is, the determined view can be specified at different levels of granularity. For example, a view can be PLAX, PLAX1, or PLAX1A, where PLAX1 is a subview of PLAX, and PLAX1A is a subview of PLAX1. PLAX1 further refines or delineates PLAX and PLAX1A further refines or delineates PLAX1. Each refinement or delineation can correspondingly refine or delineate anatomy present in the view.

Values of data elements, such as of the view 200, the anatomy 210, the usability statistics 230 or combinations thereof can be included in the displayed subset 152. In some embodiments, the values of the view 200, the anatomy 210 and the usability statistics 230 are omitted from the display. The values of the measurement data element 220 or representations thereof are included in the display, such as LVEF, IVC Diam, and the like. Representations of the measurement data element 220 can include abbreviations, icons, or other indicators.

The values or instances of the measurement data element 220 for the subset 152 are displayed in the selectable list. The data elements illustrate the relationship between values of the view/subview 200 that are mapped to values of the anatomy 210, and values of the anatomy 210 are mapped to measurements included in the subset 152. The values of the anatomy are portions of the heart anatomy, such as left ventricle, left atrium, aorta, mitral value, aortic valve, sub anatomical portions or each, combinations of each, and the like. In some embodiments, the heart anatomy can include a phase, such as left ventricle end-diastolic.

In some embodiments, the subset 152 is ordered according to usability statistics 230 or combinations of usability statistics 230 and anatomy 210. For example, a measurement within a highest frequency of use is displayed first. In another example, measurements are ordered within anatomy 210. For example, measurements mapped from the anatomy of the left ventricle are ordered by frequency and grouped together, and measurements of the right ventricle are ordered by frequency and grouped together. In some instances, the context is based on the view and in some instances the context is based on combinations of the view and usability statistics.

Figure 3:
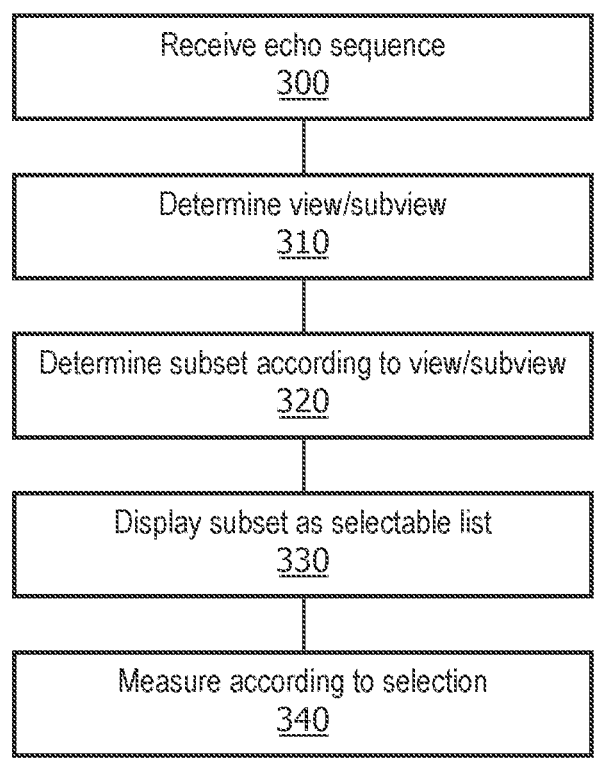
FIG. 3 illustrates an example of a displayed echocardiogram sequence with a context based view of measurements.

With reference to FIG. 3, an embodiment of a method of context based view of echocardiogram measurements is flowcharted.

At 300, an echocardiogram sequence 110 is received. The echocardiogram sequence 110 can be received directly from the US imaging scanner 120 or from computer memory or storage.

At 310, a view of the sequence 110 is determined. The determined view can include sub-views. In some embodiments, the view is determined by analysis of the ultrasound image data. The analysis can include pattern matching of the pixel data with reference images. The analysis can include segmentation of anatomical features and comparison with an anatomical model. In some embodiments, the view is determined by manual review and/or input.

At 320, a subset 152 of measurements is determined from the list of echocardiogram measurements according to the view and a mapping 154 between the view and the subset 152. The mapping 154 includes a first sub-mapping from the view to portions of heart anatomy within the view, and a second sub-mapping from portions of heart anatomy within the view to the subset 152 of measurements. A lookup table can store the mappings between the views and the measurements. The lookup table includes data elements of the view and the mapped measurement. The lookup table can include usability statistics 230. The usabilities statistics can be according to system, organization, site, user or combinations thereof. For example, in a PLAX view, use can be tracked, such as a total number or a percentage frequency of the LVEF being measured in the PLAX view, a total number or a percentage frequency of the LVEF being measured by a current user in the PLAX view, and the like.

At 330 the determined subset 152 of measurements in a selectable list and the view of the ultrasound imaging sequence are displayed on the display device 162. The displayed subset 152 can be ordered according to the usability statistics. For example, the determined subset 152 of measurements can be ordered to a total number or a percentage frequency of use in the displayed subset 152

At 340, in response to an input from the input device 132, an aspect of the heart in the view is measured according to a selected measurement in the displayed subset of measurements. For example, a user selects the LVEF with a mouse click, the LVEF is measured according to the received sequence 110.

In some embodiments, steps 330 and 340 are omitted, and at least one measurement of the subset of measurements is selected and applied to the view of the ultrasound imaging sequence autonomously. For example, a measurement is designated as autonomous within a view, such as LVEF within PLAX according to a site policy or the usability statistics. Autonomous measurements can be indicated in the lookup table, such as with a separate data element with a binary value. The autonomous measurement is applied to the received sequence 110 prior to displaying the received sequence 110, such as upon being received.

The above may be implemented by way of computer readable instructions, encoded or embedded on a computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention is constructed as including all such modifications and alterations insofar as they come within the scope of the appended claims or the equivalents thereof. The word "comprising" does not exclude other elements or steps, and the indefinite article "a" or "an" does not exclude a plurality.

The invention claimed is:

1. A method, comprising:
 storing a mapping that maps each image view of a plurality of different image views to one or more types of measurements of a plurality of different types of measurements, wherein the one or more types of measurements for a particular image view of the plurality of different image views are applicable to be computed from the particular image view and represent a subset of the plurality of different types of measurements;
 determining the subset of the plurality of different types of measurements for the particular image view from the mapping, wherein measurements of the plurality of different types of measurements not in the subset are not applicable to an anatomy in the particular image view;

displaying the particular image view and the determined subset of the plurality of different types of measurements with a display, wherein the plurality of different types of measurements are displayed in a user selectable list;
receiving an input selecting one of the displayed types of measurements in the list; and
computing a value for the selected type of measurement based on the anatomy in the particular image view, wherein the different types of measurements are used to one or more of monitor or diagnose one or more of a heart disease or a heart condition.

2. The method according to claim 1, further including:
mapping each of the image views to the anatomy in the particular image view; and
displaying the particular image view, comprising the determined subset of the plurality of different types of measurements and the anatomy.

3. The method according to claim 1, wherein the image view includes pixels that represent at least a left ventricle of a heart of a subject and the selected type of measurement is left ventricular ejection fraction.

4. The method according to claim 3, wherein the subset of the type of measurements does not include a diameter of an inferior vena cava of the heart of the subject, wherein the particular image view does not include pixels that represent the inferior vena cava of the heart of the subject.

5. A non-transitory computer readable medium encoded with computer readable instructions, which, when executed by a processor, cause the processor to:
store a mapping that maps each image view of a plurality of different image views to one or more types of measurements of a plurality of different types of measurements, wherein the one or more types of measurements for a particular image view of the plurality of different image views are applicable to be computed from the particular image view and represent a subset of the plurality of different types of measurements;
determine the subset of the plurality of different types of measurements for the particular image view from the mapping, wherein measurements of the plurality of different types of measurements not in the subset are not applicable to an anatomy in the particular image view;
display the particular image view and the determined subset of the plurality of different types of measurements with a display, wherein the plurality of different types of measurements are displayed in a user selectable list;
receive an input selecting one of the displayed types of measurements in the list; and
compute a value for the selected type of measurement based on the anatomy in the particular image view, wherein the different types of measurements are used to one or more of monitor or diagnose one or more of a heart disease or a heart condition.

6. The non-transitory computer readable medium of claim 5, wherein executing the computer readable instructions further cause the processor to:
map each of the image views to the anatomy in the particular image view;
display the particular image view, the determined subset of the plurality of different types of measurements, and the anatomy in the particular image view.

7. The non-transitory computer readable medium of claim 5, wherein executing the computer readable instructions further cause the processor to:
map each of the image views to the anatomy in the particular image view;
determine anatomy in the particular image view; and
determine the subset of the plurality of different types of measurements based on the anatomy in the particular image view.

8. The non-transitory computer readable medium of claim 5, wherein the particular image view includes pixels that represent at least a left ventricle of a heart of a subject and the selected type of measurement is left ventricular ejection fraction.

9. The non-transitory computer readable medium of claim 8, wherein the subset of the type of measurements does not include a diameter of an inferior vena cava of the heart of the subject, wherein the particular image view does not include pixels that represent the inferior vena cava of the heart of the subject.

10. A non-transitory computer readable medium encoded with computer readable instructions, which, when executed by a processor, cause the processor to:
determine which measurements from a list of possible echocardiogram measurements are applicable to anatomy in a view of an ultrasound imaging sequence based on a mapping between the view and the possible echocardiogram measurements,
wherein the determined measurements are a subset of the list of possible echocardiogram measurements, and the measurements of the list of possible echocardiogram measurements that are not applicable to any of the anatomy in the view are not included in the subset;
display the determined subset of measurements in a user selectable list and the view of the ultrasound imaging sequence on a user interface displayed on a display device; and
in response to an input selecting one of the displayed subset of measurements, measure an aspect of a heart in the view according to the one selected displayed subset of measurement, wherein the different types of measurements are used to one or more of monitor or diagnose one or more of a heart disease or a heart condition.

11. The non-transitory computer readable medium of claim 10, wherein executing the computer readable instructions further cause the processor to:
map a first sub-mapping from the view to portions of the heart within the view; and
map a second sub-mapping from the portions of heart anatomy within the view to the subset of measurements.

12. The non-transitory computer readable medium of claim 10, wherein executing the computer readable instructions further cause the processor to:
display only the determined subset of measurements in the selectable list and not display a remainder of the list of measurements in the selectable list.

13. The non-transitory computer readable medium of claim 10, wherein executing the computer readable instructions further cause the processor to:
determine the view from an analysis of the ultrasound imaging sequence.

14. The non-transitory computer readable medium of claim 10, wherein executing the computer readable instructions further cause the processor to:
store the list of echocardiogram measurements as a lookup table that comprises elements representing different measurements according to corresponding views.

15. The non-transitory computer readable medium of claim 14, wherein executing the computer readable instructions further cause the processor to:
  order the displayed subset of measurements according to usability statistics.

16. The non-transitory computer readable medium of claim 10, wherein executing the computer readable instructions further cause the processor to:
  select and apply at least one measurement of the subset of measurements to the view of the ultrasound imaging sequence autonomously.

* * * * *